United States Patent
James et al.

(10) Patent No.: US 9,983,099 B2
(45) Date of Patent: May 29, 2018

(54) ANALYTICAL INSTRUMENT WITH TEMPORAL CONTROL OF ION MOBILITY SPECTROMETER CONTROL PARAMETERS

(75) Inventors: Robert T. James, Newmarket (CA); Volodimir Bondarenko, Mississauga (CA); Reno Debono, Clinton, NJ (US); Julian Burton, Franklin Park, NJ (US); John Carroll, Madison, NJ (US)

(73) Assignee: SMITHS DETECTION MONTREAL INC., Laval, Quebec (CA)

( * ) Notice: Subject to any disclaimer, the term of this patent is extended or adjusted under 35 U.S.C. 154(b) by 1480 days.

(21) Appl. No.: 12/997,358

(22) PCT Filed: Jun. 10, 2009

(86) PCT No.: PCT/US2009/046820
§ 371 (c)(1),
(2), (4) Date: May 25, 2011

(87) PCT Pub. No.: WO2009/152198
PCT Pub. Date: Dec. 17, 2009

(65) Prior Publication Data
US 2011/0223674 A1    Sep. 15, 2011

Related U.S. Application Data

(60) Provisional application No. 61/129,246, filed on Jun. 13, 2008.

(51) Int. Cl.
*G01N 27/62* (2006.01)
*G01N 35/00* (2006.01)
(Continued)

(52) U.S. Cl.
CPC ............ *G01N 1/02* (2013.01); *G01N 27/622* (2013.01); *G01N 35/00584* (2013.01);
(Continued)

(58) Field of Classification Search
None
See application file for complete search history.

(56) References Cited

U.S. PATENT DOCUMENTS

| | | |
|---|---|---|
| 5,068,533 A | 11/1991 | Grossman et al. |
| 2002/0134933 A1* | 9/2002 | Jenkins ............... G01N 27/622 250/287 |

(Continued)

FOREIGN PATENT DOCUMENTS

| | | |
|---|---|---|
| WO | WO-2006/061593 A2 | 6/2006 |
| WO | WO-2007/079234 A2 | 7/2007 |

(Continued)

OTHER PUBLICATIONS

International Search Report in PCT/US2009/046820 dated Jun. 4, 2010.

(Continued)

*Primary Examiner* — Christopher Adam Hixson
*Assistant Examiner* — Michelle Adams
(74) *Attorney, Agent, or Firm* — Foley & Lardner LLP

(57) ABSTRACT

An ion mobility spectrometer analytical instrument, including an ion mobility spectrometer, a swab interface, and a desorber assembly. The desorber assembly includes a heat transfer device configured to heat a desorber, as well as a supply configured to direct gas through the desorber. The instrument further includes a drift tube, high voltage device arrayed, at least in part, proximate to the drift tube, wherein the high voltage device is configured to change a polarity of a voltage applied to the drift tube and have an absolute voltage of about 500 to 1500 volts. The instrument further includes a reactant supply unit adapted to supply reactant during a sample substance analysis, and a control unit.

12 Claims, 5 Drawing Sheets

(51) Int. Cl.
*G01N 1/02* (2006.01)
*G01N 1/40* (2006.01)

(52) U.S. Cl.
CPC .................. *G01N 2001/028* (2013.01); *G01N 2001/4038* (2013.01); *G01N 2035/0097* (2013.01); *Y10T 436/115831* (2015.01)

(56) References Cited

U.S. PATENT DOCUMENTS

| | | | |
|---|---|---|---|
| 2003/0153844 A1* | 8/2003 | Smith | A61B 10/0051 |
| | | | 600/573 |
| 2005/0051719 A1* | 3/2005 | Miller | G01N 27/622 |
| | | | 250/287 |
| 2005/0205673 A1* | 9/2005 | Morris | B01L 3/5027 |
| | | | 235/385 |
| 2007/0217949 A1* | 9/2007 | Mimura | G01N 35/00603 |
| | | | 422/63 |
| 2008/0017791 A1 | 1/2008 | Wilks et al. | |
| 2008/0101995 A1* | 5/2008 | Gabowitcz et al. | 422/99 |

FOREIGN PATENT DOCUMENTS

| | | |
|---|---|---|
| WO | WO-2007/089221 | 8/2007 |
| WO | WO-2008/035138 A2 | 3/2008 |

OTHER PUBLICATIONS

AT-AO-6/10 User Manual, Part No. 320379-01, National Instruments Corporation, Sep. 1994 Edition.

Official Communication issued in corresponding EP Patent application No. 09763488.5 dated Jan. 10, 2017.

\* cited by examiner

ANALYTICAL INSTRUMENT WITH TEMPORAL CONTROL OF ION MOBILITY SPECTROMETER CONTROL PARAMETERS

CROSS-REFERENCE TO RELATED APPLICATIONS

This application claims priority to U.S. Patent Application No. 61/129,246, filed Jun. 13, 2008, the entire contents of which is hereby incorporated by reference in its entirety.

BACKGROUND

Ion mobility spectrometer detectors are used to detect the presence of materials of concern in an environment. A library of known materials of concern is created and, during use of the detector, measurements known for these materials are compared with the measurement results from, for example, a test swab brought into contact with a component suspected of being contaminated with one or more materials of concern, in an effort to determine whether the exemplary test swab is contaminated with a material of concern.

SUMMARY

In a first exemplary embodiment of the present invention, there is an ion mobility spectrometer analytical instrument, comprising an ion mobility spectrometer, a swab interface, a desorber assembly, wherein the desorber assembly includes a heat transfer device adapted to heat a desorber, and wherein the desorber assembly includes a gas supply adapted to direct gas through the desorber, a drift tube, a high voltage device arrayed, at least in part, proximate to the drift tube, wherein the high voltage device is adapted to change a polarity of a voltage applied to the drift tube and have a voltage gradient of the drift tube of about 100 to 500 volts per centimeter (in some embodiments, a high voltage power supply provides four (4) voltages to the drift tube: source voltage, fixed grid voltage, gating (modulating) grid voltage and guard voltage (the source, fixed grid and gating grid have absolute voltage values in the neighborhood of 1600 to 2000 V, the guard voltage is around 80-90 V); a reactant supply unit adapted to supply reactant during a sample substance analysis, and a control unit which includes a data input and storage assembly adapted to receive, via at least one of an analogue and a digital data communication port, and store, a first fragment including at least a first analytical instrument control parameter, wherein the data input and storage assembly is adapted to permit the first fragment to be superseded by a second fragment.

In another exemplary embodiment, there is an analytical instrument as described above or below, comprising a substance detector adapted to perform an analysis on a sample substance, the substance detector including an ion mobility spectrometer (IMS), a control unit, and a data input and storage assembly adapted to receive, via at least one of an analogue and a digital data communication port, and store: a first fragment, the first fragment including at least a first analytical instrument control parameter, and a second fragment, the second fragment including at least a second analytical instrument control parameter, wherein the control unit is adapted to control, during a first temporal period of a sample substance analysis, operational functionality of the analytical instrument based on at least the stored first fragment, and wherein the control unit is adapted to, during a second temporal period later than the first temporal period, control the operational functionality of the analytical instrument based on at least the stored second fragment. In another exemplary embodiment, there is an analytical instrument as described above or below, wherein the substance detector includes a desorber, and wherein the operational functionality of the analytical instrument controlled during the first temporal period is a setpoint of the desorber, and wherein the control unit is adapted to control the setpoint of the desorber based on the first analytical instrument control parameter.

In another exemplary embodiment, there is an analytical instrument as described above or below, wherein the control unit is adapted to, based on the first and second analytical instrument control parameters, respectively: control the desorber to have a first setpoint based on the first analytical control parameter, during the first temporal period; and control the desorber to have a second setpoint, different from the first setpoint, based on the second analytical control parameter, during the second temporal period.

In another exemplary embodiment, there is an analytical instrument as described above or below, wherein the substance detector includes a desorber and an IMS gate, wherein the first fragment includes a third analytical instrument control parameter, wherein operational functionality of the analytical instrument controlled during the first temporal period is a setpoint of the desorber and a width of time of IMS gate opening, and wherein the control unit is adapted to control the setpoint of the desorber and the width of time of the ISM gate opening based on the first analytical instrument control parameter and the third analytical instrument control parameter, respectively. In another exemplary embodiment, there is an analytical instrument as described above or below, wherein the substance detector includes a desorber and an IMS gate, wherein the first fragment includes a plurality of respective analytical instrument control parameters including the first analytical instrument control parameter, wherein the second fragment includes a plurality of respective analytical instrument control parameters including the second analytical instrument control parameter, wherein the control unit is adapted to, during the first temporal period, based on the plurality of respective analytical instrument control parameters included in the first fragment: control the desorber to have a first setpoint and control a width of gate opening of the IMS gate to have a first opening width based on the respective analytical instrument control parameters of the first fragment, and wherein the control unit is adapted to, during the second temporal period, based on the plurality of respective analytical instrument control parameters included in the second fragment: control the desorber to have a second setpoint different from the first setpoint and control a width of gate opening of the IMS gate to have a second opening width different from the first opening width based on the respective analytical instrument control parameters of the second fragment.

In another exemplary embodiment, there is an analytical instrument as described above or below, wherein the first and second fragments include a plurality of respective analytical instrument control parameters which include one or more of: a control parameter to control a setpoint of a desorber of the analytical instrument during operation of the analytical instrument; a control parameter to control desorber flow of the desorber during operation of the analytical instrument; a control parameter to control a width of an IMS gate opening time to control sensitivity and/or resolution during operation of the analytical instrument; a control parameter to control a polarity of a voltage applied to a drift tube of the IMS during operation of the analytical instrument (note that in some embodiments, a magnitude of the voltage can also be changed, although typically, this change is accomplished by re-hard coding the instrument (i.e., a fragment is not used), although in some embodiments, a fragment may be used); a control parameter to control reactant usage during operation of the analytical instrument; a control parameter to control a sample substance purge cycle during operation of the analytical instrument; a control parameter to control the analytical instrument to collect data during the sample substance purge cycle to verify whether the sample substance has been sufficiently purged from a test location of the substance detector of the analytical instrument; and control parameter to control the analytical instrument to perform a diagnostic routine, the diagnostic routine including a routine enabling the analytical instrument to make a determination of whether the reactant is present, wherein the analytical instrument is adapted to be controlled to operate based on one or more of the control parameters of the first and second fragments.

In another exemplary embodiment, there is an analytical instrument as described above or below, wherein the plurality of respective analytical instrument control parameters of the first and second fragments include one or more of: a control parameter to control desorber flow of the desorber during operation of the analytical instrument while switching polarity of the voltage applied to the drift tube during an analysis of a sample substance.

In another exemplary embodiment, there is an analytical instrument as described above or below, wherein the first and second fragments include a plurality of respective analytical instrument control parameters, wherein the analytical instrument is adapted to operate in an operational regime, wherein operation of the analytical instrument in the operating regime includes a sample substance analysis operation and an idle operation, and wherein the analytical instrument is adapted to variously implement various of the respective analytical instrument control parameters depending on whether the analytical instrument is undertaking a sample substance analysis operation or undertaking an idle operation, and wherein, when the analytical instrument is undertaking an idle operation, the analytical instrument analyzes a calibration substance for calibration purposes separate from the sample substance. In another exemplary embodiment, there is an analytical instrument as described above or below, wherein the analytical instrument has an IMS drift tube, and wherein the analytical instrument is adapted to adjust the value of a voltage applied to the drift tube. In another exemplary embodiment, there is an analytical instrument as described above or below, wherein the substance detector includes a desorber; the substance detector includes an IMS drift tube, the substance detector being adapted to switch, during an analysis of the sample substance, polarities of a voltage applied to the drift tube according to a polarity switching regime, the polarity switching regime being based on one or more analytical instrument control parameters of at least one of the first fragment and the second fragment; the analytical instrument is adapted to vary a temperature ramping regime of the desorber, wherein the control unit is adapted to control desorber temperature to achieve one or more temperatures during a sample analysis time period according to a prestored temperature ramping regime, the prestored temperature ramping regime being stored in the data input and storage assembly and being based on one or more analytical instrument control parameters of at least one of the first fragment and the second fragment; the analytical instrument is adapted to enter at least one desorber flow control regime, wherein, when the desorber flow control regime is entered, the control unit controls a desorber flow to achieve one or more desorber flows during the sample analysis time period according to a prestored desorber flow control regime, the prestored desorber flow control regime being stored in the data input and storage assembly and being based on one or more analytical instrument control parameters of at least one of the first fragment and the second fragment; the analytical instrument is adapted to enter at least one reactant flow control regime, wherein, when the reactant flow control regime is entered, the control unit controls a reactant flow to variously permit reactant flow and halt the reactant flow during the analysis of the sample substance according to a prestored reactant flow regime, the prestored reactant flow regime being stored in the data input storage assembly and being based on one or more analytical instrument control parameters of at least one of the first fragment and the second fragment; and the analytical instrument is adapted to enter at least one purge control regime, wherein, when the at least one purge control regime is entered, the analytical instrument purges a sample substance containment area effectively of all sample substance according to a prestored purge control regime, the prestored purge control regime being stored in the data input and storage assembly and being based on one or more analytical instrument control parameters of at least one of the first fragment and the second fragment.

DETAILED DESCRIPTION OF SOME EMBODIMENTS

Figure 1:
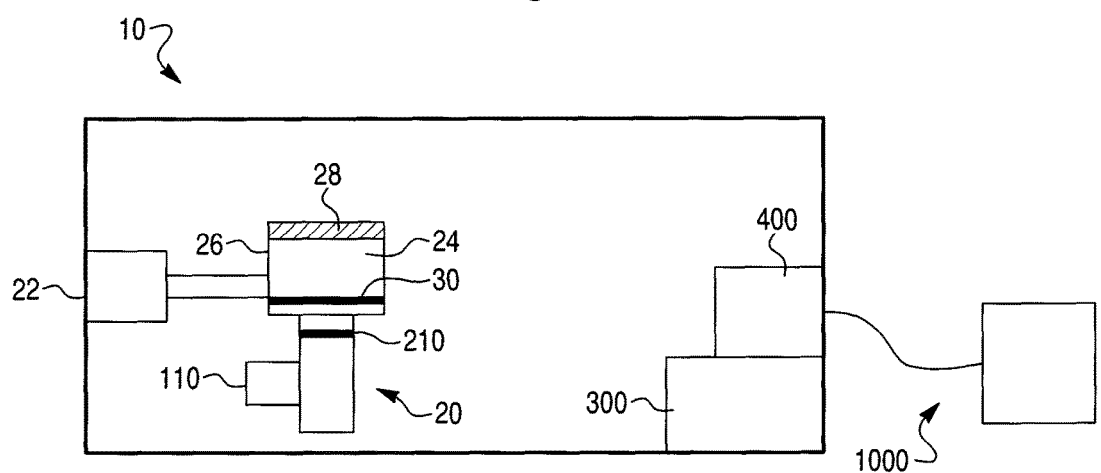
FIG. 1 schematically illustrates an analytical instrument according to an embodiment of the present invention.

In an embodiment of the present invention, there is an analytical instrument 10 including an ion mobility spectrometer (IMS) 20 that includes an ionization source, an ion reaction region, an ion drift region (e.g. in the form of a tube), an ion injection gate (shutter and/or grid, etc.) interposed between the ion reaction region and the ion drift region, and an ion detector. The analytical instrument 10 further includes a swab interface 22, and a desorber assembly 24, wherein the desorber assembly includes a heat transfer device 26 adapted to heat a desorber 28, and wherein the analytical instrument 10 includes a device 29 adapted to direct a gas towards the desorber 28. The exemplary embodiment operates at atmospheric pressure where the mean free path of contained gas molecules in the drift region is a small fraction of the dimensions of the container, although in other embodiments, different pressures and/or different ratios may exist. A carrier gas, normally purified atmospheric air (particularly purified to remove water vapor which can interfere with the detection of certain types of charged species) is introduced into the ion mobility spectrometer with a sample substance of the material whose identity is to be determined by characterization of its ion mobility properties. The carrier gas containing a sample substance is introduced through an inlet so as to be exposed to the ionization source. This causes portions of both the carrier gas and the sample substance to be directly ionized at the ionization source. The molecules of the carrier gas are typically present in far greater numbers than the sample material and so more of these are ionized. The gaseous mixture is located within the reaction region at this stage and multiple collisions between the molecules of the carrier and the sample gas(es) occur, the result of which is that the ion charge tends to be transferred by these collisions from the carrier molecules to molecules of the sample substance, thus resulting in a secondary ionization process which ionizes an increased number of the molecules of the sample substance. The reaction region is sometimes arranged to be under the influence of a potential gradient which moves the charged mixture towards an ion injection grid which is electrically charged to prevent/reduce transfer of ions from the reaction region to the drift region but which can be deenergized so as to let a pulse of ions pass through into the drift region. Accordingly, in some embodiments, periodically, the grid is de-energized for a short time and a number of ions are introduced into the drift region. This period is called the grating time and can be varied. Hereinafter, this grid is referred to as a "gate." In this regard, any device which accomplishes the task of sufficiently controllably blocking and admitting ions may be used to practice some embodiments of the invention, and will be considered a "gate."

In general, the ion mobility spectrometer utilized in some embodiments of the present invention ionizes molecules of a sample substance by using a radioactive source, such as $^{63}$Ni or $^{241}$Am, or using some other type of ionizing source. The ions are then passed into a drift tube at specified intervals by means of a gating mechanism. Ions in the drift tube are subjected to a homogeneous/quasi-homogeneous electric field that drives the ions through the drift tube. As the ions pass through the drift tube, they interact with neutral drift molecules as they pass towards a detector. Due to differences in ion mass, size, and shape, the ions arrive at the detector at a different time. The detector records the ions as they reach the detector, and the resulting signal is characteristic of the chemical composition of the sample.

Specifically, the drift region is arranged to be under the influence of an electrostatic drift field or potential gradient which acts to move ions in the drift region down the tube away from the ion injection grid towards a detector electrode which collects the charge from the ions and is located at the end of the drift region. The time of arrival of each ion at the detector grid relative to the time that the ion injection gate was opened is determined by the mobility of the ion in the carrier gas occupying the drift region. Larger ions move more slowly through the drift region and take longer to travel to the detector than smaller ions. Ions with the same mobility have their velocities modified slightly due to diffusion effects; when they arrive at the detector electrode they are spread in an error function, the peak of which enables one to determine the time taken between the opening of the grid and arrival of the group at the detector. This can be used, in some embodiments, to characterize the ions.

In an exemplary embodiment of the present invention, the analytical instrument 10 includes a sample material membrane 30, sample substance material passing from the sample side through the membrane 30 to the IMS side to be exposed to an ionization source.

In an exemplary embodiment present invention, the analytical instrument is provided with an alternating potential to the ionization source. In some embodiments, applying an alternating potential to the radioactive sources may remove the effects of surface charge build-up on the various components in the ionization and reaction regions. The concentration of ions in these regions is much greater than that in the rest of the device and, if a constant voltage is applied to the source, collision of ions with surfaces in this region may lead, over a period of seconds or greater, to the build-up of charge on the surfaces. This may result in the electric field within the device being modified so as to repel ions away from the desired paths. The observed effect may be a steady reduction in signal amplitude with time.

The alternating potential may be altered in frequency and/or in amplitude; the rectangular waveform may be variable in symmetry with the respect to the positive and negative such that the duration and amplitude of the positive potential may be varied independently of the duration and amplitude of the negative potential. In this way ion residence times may be varied for ions in the reaction region enabling the target ion concentration to be maximized independently for positive and negative ions.

In view of the above, operationally, in an embodiment of the present invention, the method of using an ion mobility spectrometer includes utilizing not only an alternating potential on the ionization source but also one or more drift tubes 100 (sometimes, a pair of alternately opposed drift tubes), allowing a sample material from the reaction region to enter a drift region by application of a short gate opening pulse to the ion injection gate (shutter or grid etc.), the time delay between the start of one half-cycle of the alternating potential and the gate opening pulse being varied in a number of preliminary steps and the consequent currents, detected at the ion detector in the drift tube, being stored in a memory device, until at the end of one or more preliminary steps, followed by selecting an adequate time delay for the gate-opening pulse for subsequent testing believed to provide adequate, if not optimum results, e.g. maximum amplitude of the ion peak being assessed, for the ions on which the preliminary steps were carried out. Along these lines, the time of gate opening may be referred to as the "width of gate opening time", etc. Further along these lines, opening of the gate, one or more times, for a desired width of gate opening time, may be referred to as "operating the IMS gate at a gate width timing."

In some embodiments, the test may be performed under the control of a microprocessor in a control unit/controller 300, which is preprogrammed to perform the preliminary steps and the subsequent testing.

A drift region of tubular configuration may be constructed of alternating rings of ceramic material and metal, these electrically conductive metal rings being called drift rings (sometimes called herein "guard rings"). The stack of rings is clamped together and sealed so as to make a gas tight tube. Devices of this type often enclose the stack of rings within an outer sealed envelope. The electrostatic drift field potential gradient is established by connecting adjacent drift rings to each other via a resistor and connecting the end guard rings to the terminals of a voltage source 110. The conductive rings afford a series of ascending voltage levels and the longitudinal axis of the tube coincides with the longitudinal axis of the electrostatic field which is thus established.

In some embodiments, the IMS operates with a positive or negative potential of, for example, 1250 V, more or less (e.g., 1000 V, 1100 V, 1200 V, 1300 V, 1400 V, and any increment there between, etc.). In some embodiments, the voltage is about 2000 V, more or less. Any voltage that will permit the IMS device to operate as desired may be used to practice some embodiments of the invention. In some embodiments, this potential may be adjusted after the analytical instrument is made/enters use in the field, etc., permitting optimization of the voltage.

During operation of an exemplary embodiment, drift tube gas, typically dried purified air, is circulated though the one or more drift tubes. In some embodiments, 1 to 50 $cm^3$ per minute of gas per $cm^3$ of drift tube is utilized. In some embodiments, 200 $cm^3$ per minute, 300 $cm^3$ per minute, 400 $cm^3$ per minute, etc., may be used. The carrier gas, which in a typical use is ambient atmospheric air, containing a gas sample to be detected and characterized is drawn into the inlet by a pump attached to a vent. Similar flow rates in relation to the volume of the reactant tube may be used as for the drift gas.

The membrane 30 may be selectively permeable to species desired to be detected. The species desired to detect thus permeate through the membrane into the ionization tube and together with some of the carrier gas pass into the vicinity of the ionizing source. The membrane may comprise a sheet of silicone-based rubber material such as dimethyl silicone rubber. The voltage sources are switched on, and the carrier gas molecules are ionized and to a lesser extent the sample species.

As the ion mobility spectrometer operates at or near atmospheric pressure, the mean free path of the ions and other molecules is small in relation to the dimensions of the confining space and there are many collisions between the various gas molecules in the reaction region. The collisions tend to produce ionized sample molecules by charge transfer from the ionized carrier gas molecules.

The membrane 30 may serve a variety of functions, such as protecting the interior of the device from moisture, preventing contaminants from entering the device, and increasing sensitivity.

In operation, a sample is applied to one side of the membrane (sample side) and analyte passes through the membrane to reach the other side of the membrane (IMS side) from which analyte is taken for analysis. The sample can be applied to the analyte in a variety of ways. For example, sample can be directly contact with the membrane. In the alternative, a swab containing sample can be placed in proximity to the membrane and the sample thermally desorbed to collect on the membrane. The speed at which analyte passes through the membrane is dependent on several factors, such as the thickness of the membrane, the composition of the membrane, and the composition of the sample. But a higher concentration of the analyte on the sample side results on more sample reaching the IMS side of the membrane. In some embodiments of the present invention, air flow moves the analyte from the sample source, such as a swab, and through the membrane. In some embodiments of the present invention, the detector components of the analytical instrument 10 correspond to the SABRE 4000™ produced by Smiths Detection™, the performance characteristics, operational characteristics and/or the major components thereof being usable in the analytical instrument 10 according to some embodiments of the present invention, the design and all of the just mentioned characteristics and components of the SABRE 4000™ being incorporated herein by reference in their entirety.

In an exemplary embodiment of the present invention, the control unit 300 of the analytical instrument 10 includes a data input and storage assembly 400 adapted to receive data via at least one of an analogue and a digital data communication port, and store, data downloaded from a remote data promulgation unit 1000 (e.g., a PC, etc.), discussed in greater detail below. In some embodiments, the data input and storage assembly (DISA) 400 includes an ethernet unit (wire and/or wireless), a USB connection, SD card slot, software interface, etc. In some embodiments, the DISA 400 allows for the downloading of data without a PC. In some embodiments, the DISA 400 is WiFi compatible. Any device, method or system which may be used to download data to the analytical instrument 10 in lieu of a hard-coded algorithm swap-out (e.g., changing out chips, etc.) may be used to practice some embodiments of the invention.

Figure 2:
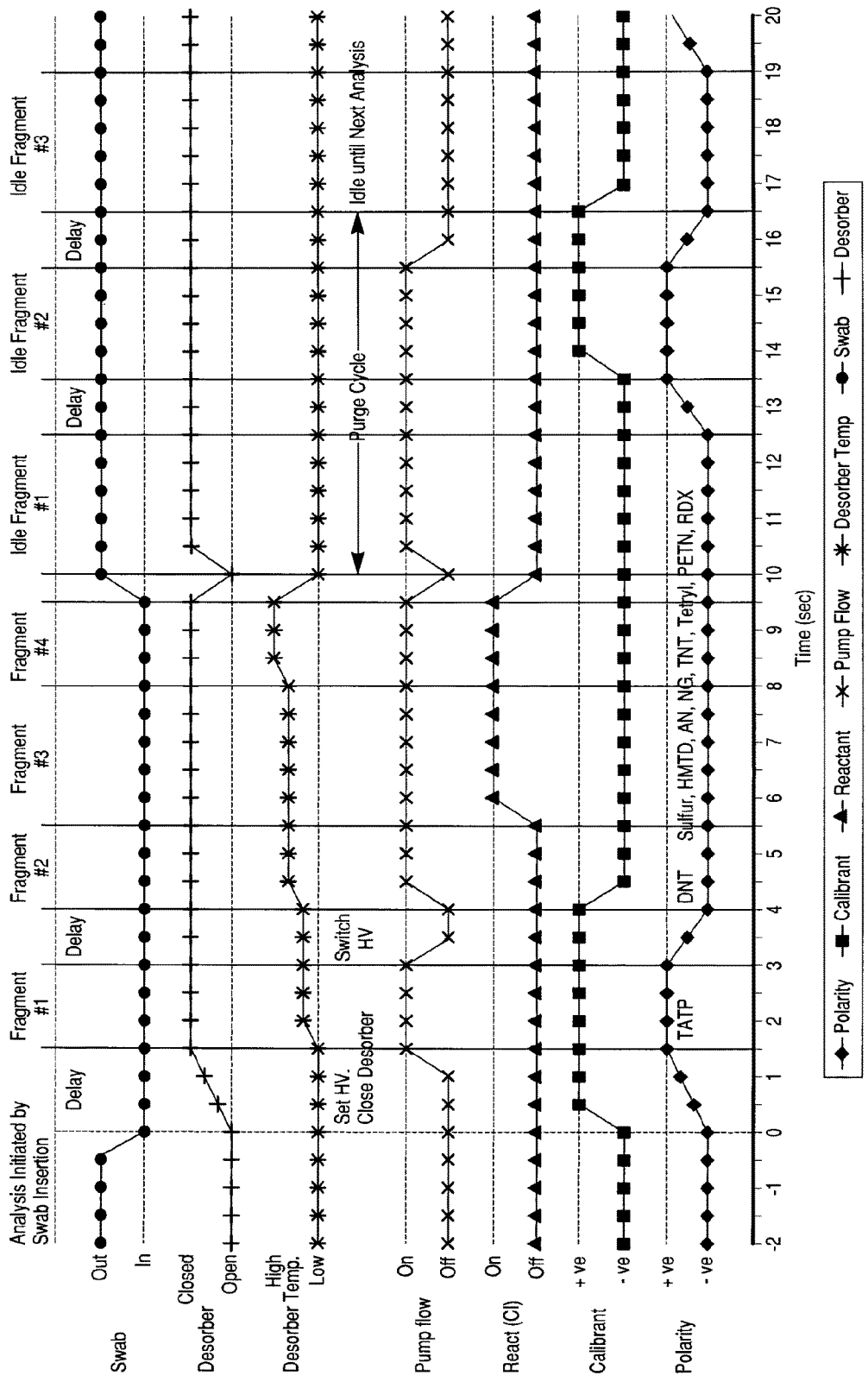
FIG. 2 presents a chart illustrating multiple fragments with multiple control parameters according to an embodiment of the present invention.

The analytical instrument 10 may have stored in the DISA 400, having been downloaded into the DISA 400 from a remote PC, one or more fragments which include analytical instrument control parameters. The control unit 300 is adapted to control, during respective distinct periods of time of a sample substance analysis (an analysis of a sample substance using the analytical instrument 10), operational functionality of the analytical instrument based on the stored fragments. In an exemplary embodiment of the present invention, a first fragment may be data which is used by the control unit 300 to direct various components of the analytical instrument 10 to operate as shown in FIG. 2, with reference to "Fragment #1." In an exemplary embodiment, multiple fragments may be stored in DISA 400. In this regard, FIG. 2 presents a chart showing, when the analytical instrument 10 is used to detect explosives, how various components of the analytical instrument operate across the multiple fragments. In some embodiments, a fragment may be thought of as a defined subset of an analysis which independently defines instrumental, temporal and detection parameters, relative to other subsets.

In an exemplary embodiment, a first fragment stored in the DISA 400 may be used by the control unit 300 to set up an operational functionality of the analytical instrument 10 during a time period of a sample substance analysis such that the desorber 22 has a setpoint such that it heats to 150 degrees C. That is, the control unit 300 is configured to control a setpoint of the desorber 22 based on an analytical instrument control parameter embodied in the fragment stored in the DISA 400. In this regard, if a plurality of fragments are stored in the DISA 400 (having been downloaded into the DISA 400 from, for example, a remote PC), the control unit may be configured to, based on respective analytical instrument control parameters in respective stored fragments, respectively control the desorber 22 to have a first set point during one temporal period, and control the desorber 22 to have a second setpoint, different from the first setpoint during another temporal period following the first temporal period.

As may be inferred in the just discussed scenario and/or in view of FIG. 2, the DISA 400 may have stored therein two or more fragments. In an exemplary embodiment, these fragments contain respective analytical instrument control parameters for various components of the analytical device 10. Typically, these fragments include data to control various components for specified periods of times (e.g., 3-5 seconds in length) to vary detection parameters, and typically are fashioned to be discrete (i.e., typically, they only contain data to set control parameters once for the timing of the fragment—if a control parameter is to be changed, typically, a new fragment will be entered); a control parameter leading to a change in a state of the component typically being presented in a subsequent fragment). By way of example only and not by way of limitation, in an exemplary embodiment where the analytical instrument 10 includes a desorber 22 and an IMS gate 210, the DISA 400 may include a first fragment and a second fragment. The first fragment includes two analytical instrument control parameters: a first for enabling the control unit 300 to control the setpoint of the desorber to be at a desired setpoint (as prescribed in the first fragment) during a desired length of time (as prescribed in the first fragment), the second for enabling the control unit to control an operational gate width timing of the IMS gate (as prescribed in the first fragment) within the desired length of time. If the gate width timing is to be changed before the setpoint, the gate timing will control the length of the fragment, and visa-versa.

By way of example, a DISA 400 may include a first and second fragment. The first fragment may include two analytical instrument control parameters: a first for enabling the control unit 300 to control the setpoint of the desorber to be at a desired set point during a desired length of time, and a second for enabling the control unit to control a width of timing of the IMS gate to be a timing within the desired length of time. By way of example, the first fragment may include an analytical instrument control parameter which sets the desorber set point to 120 degrees C. for four seconds, and an analytical instrument control parameter which sets the width of timing of the IMS gate to be a length of time X, at a specified temporal location within a four second long fragment. Further by way of example, the second fragment may also include two analytical instrument control parameters: a first for enabling the control unit 300 to control the set point of the desorber to be at a desired set point during a second desired length of time after the just discussed desired length, and a second for enabling the control unit to control a width of timing of IMS gate opening to be a length of time X within the desired length of time, this "new" desired length of time coming after the desired length of time prescribed in the first fragment. By way of example, the second fragment may include an analytical instrument control parameter which sets the desorber setpoint to 150 degrees C. for three seconds, and an analytical instrument control parameter which sets the width of timing of IMS gate opening to be a length of time X, at a specified temporal location within a three second long fragment.

In the just described exemplary scenario, two fragments are used. The first "sets" the setpoint of the desorber and the gate width opening timing, the second changes the setpoint of the desorber, while maintaining the gate width opening timing. (Of course, in some embodiments, the gate width opening timing could have been changed at the second fragment, and/or the setpoint of the desorber could have been held constant.) In some embodiments, serial fragments may simply maintain all control parameters.

Figure 3:
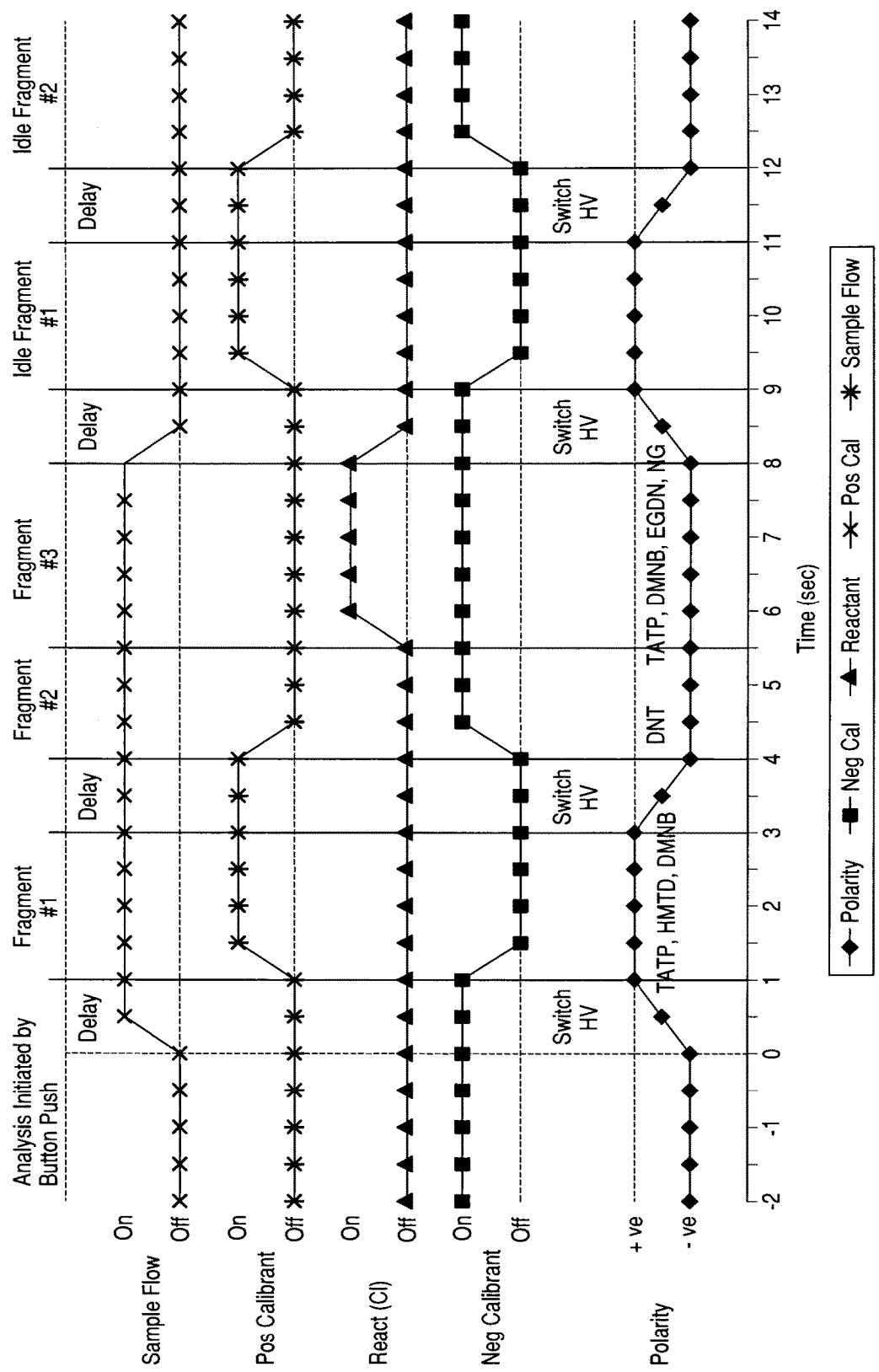
FIG. 3 presents a chart illustrating multiple fragments with multiple control parameters according to another embodiment of the present invention.

FIG. 3 presents a chart showing, when the analytical instrument 10 is placed into an explosive vapor detection mode, how various components of the analytical instrument operate across the multiple fragments. (FIG. 2, in contrast, presenting a chart for analysis of explosive sample material obtained through the use of a swab.)

As is readily understood from the Figs., in some embodiments, the number of analytical instrument operation control parameters located in a fragment are not limited to two, but instead, may include more than two control parameters. By way of example only and not by way of limitation, a fragment may include a control parameter to control a setpoint of the desorber of the analytical instrument during operation of the analytical instrument, a control parameter to control desorber flow of the desorber during operation of the analytical instrument, a control parameter to control the IMS gate width timing to control sensitivity and/or resolution during operation of the analytical instrument, a control parameter to control a polarity of a high voltage applied to a drift tube of the IMS during operation of the analytical instrument, a control parameter to control reactant usage during operation of the analytical instrument, a control parameter to control a sample substance purge cycle during operation of the analytical instrument, a control parameter to control delivery of and the type of calibrant delivered, a control parameter to control the analytical instrument to collect data during the sample substance purge cycle to verify whether the sample substance has been sufficiently purged from the analytical instrument, and/or a control parameter to control the analytical instrument to perform a diagnostic routine, the diagnostic routine including a determination of whether the reactant is present, the analytical instrument 10 being configured to be controlled to operate based on one or more of the control parameters in the fragments. Further, in some embodiments, the fragments may include control parameters to control desorber flow of the desorber during operation of the analytical instrument while switching polarity during an analysis of a sample substance.

In some embodiments of the present invention, the control unit 300 is adapted to choose between various fragments based on the results of an analytical operation of the analytical instrument. By way of example, initially, three fragments are stored in the DISA 400. The analytical instrument 10 performs an operation based on a first fragment, which results in data being obtained as a result of the control unit 300 controlling the analytical instrument to perform the operation. The control unit 300 evaluates the obtained data, and, based on this data (obtained from the operation based on the first fragment), selects one of the other two fragments on which to base a next operation, ignoring the other fragment, etc. Many more than two fragments might be available for selection after the first fragment is implemented, in some embodiments.

Further, in some embodiments, fragments may include control parameters to control a temperature of the IMS, control calibrant usage, and control the analytical instrument to operate in a "chirped gate" function.

In some embodiments, operation of the analytical instrument 10 includes performing a sample substance analysis operation and/or and an idle operation. Depending on whether the analytical instrument 10 is in a sample substance analysis mode or an idle mode, the analytical instrument 10 may variously implement various of the respective analytical instrument operational control parameters in a given fragment. For example, during a sample substance analysis, the control unit 300 of the analytical instrument will typically implement a control parameter to enable desorber flow, while in an idle mode, the control unit 300 will typically not implement a control parameter in a fragment enabling desorber flow. Conversely, while in idle mode, the control unit 300 may implement a control parameter in a fragment enabling some components which may otherwise not be utilized during a sample analysis, and visa-versa. In some embodiments, fragments are instead unique to the mode. That is, for example, in some embodiments, there are substance analysis fragments and idle fragments distinct from the substance analysis fragments.

In some embodiments of the present invention, one or more fragments may be utilized by the control unit 300 to control the analytical instrument 10 to operate in a "chirped" mode (e.g., to utilized a "chirped" transmitter/receiver methodology, where more data may be processed utilizing transforms in the frequency domain, thus obtaining a superior signal to noise ratio). Fourier Transform, Multi bit Barker codes, etc., may be used. In some embodiments, a transmitter of the analytical instrument 10, in general, and, specifically, a "transmitter" of the IMS, in such embodiments (which, in some embodiments, is an IMS gate) is open and shut at a rate different than a standard rate, sometimes in a sequence of varying durations (e.g., 01 sec, 0.005 sec, 0.001 sec etc.) (hence the term "chirped")) and data is pulled out of the signal at a receiver end because the system knows what the "transmitter" was doing in time. Along these lines, one or more fragments may be utilized by the control unit 300 to set the drift tube into a set of conditions such that the IMS gate is varied in a frequency domain, resulting in higher signal to noise.

In some embodiments, at noted above, the analytical instrument is configured to switch, during an analysis of the sample substance, polarities of a high voltage applied to the drift tube according to a polarity switching regime. The polarity switching regime is based on one or more analytical instrument control parameters of one or more of the fragments stored in the DISA 400. That is, the polarity switching regime may be based on a control parameter of a single fragment and/or the control parameters of multiple fragments, those fragments sometimes being sequential. Thus, the fragments may be used to base various control regimes, those various control regimes sometimes being complex control regimes. Further, the analytical instrument may be configured to vary a temperature ramping regime of the desorber of the analytical instrument 10. Here, the control unit controls desorber temperature to achieve one or more temperatures during a sample analysis time period according to a prestored temperature ramping regime, the prestored temperature ramping regime being stored in the data input and storage assembly and being based on one or more analytical instrument control parameters of at least one of the first fragment and the second fragment. Other analytical components/routines of the analytical instrument 10 may be so controlled based on fragments stored in the DISA 300, as would readily be understood (e.g., desorber flow control, purge control, etc.)

The DISA 300 provides for versatility of the analytical instrument 10 in the area of reconfiguring the instrument 10. In this regard, an embodiment of the present invention includes a method of reconfiguring the analytical instrument 10. This method entails, of course, obtaining a reconfigurable analytical instrument including an ion mobility spectrometer, a control unit and at least one of an analogue and a digital data storage unit, which may be part of the DISA 300. A technician places the data storage unit into communication with a remote fragment promulgation unit, depicted by way of example only in FIG. 1 as element 1000, and may be, by way of example only and not by way of limitation, a PC or the like. Communication is digital or analogue, and may be accomplished by use of an ethernet system, USB, etc. The technician utilizes the remote fragment promulgation unit 1000 to transfer data indicative of and/or sufficient to construct one or more fragments that include one or more analytical instrument control parameters. One or more fragments are then stored in the DISA 300, either having been directly downloaded from the PC (i.e., the fragments were already created in the PC), or having been constructed in the analytical instrument 10 after receipt of data sufficient to construct one or more fragments, or a combination of the two, etc. These fragments now stored in the DISA 300 may then be used by the control unit as a basis from which to control operational functionality of the analytical instrument. As may be understood, a PC may be utilized by a technician (especially a chemist) to create fragments which are then downloaded into the instrument 10, and or may be used to create building blocks which may be downloaded into the instrument 10, which are then assembled into fragments.

Figure 4:
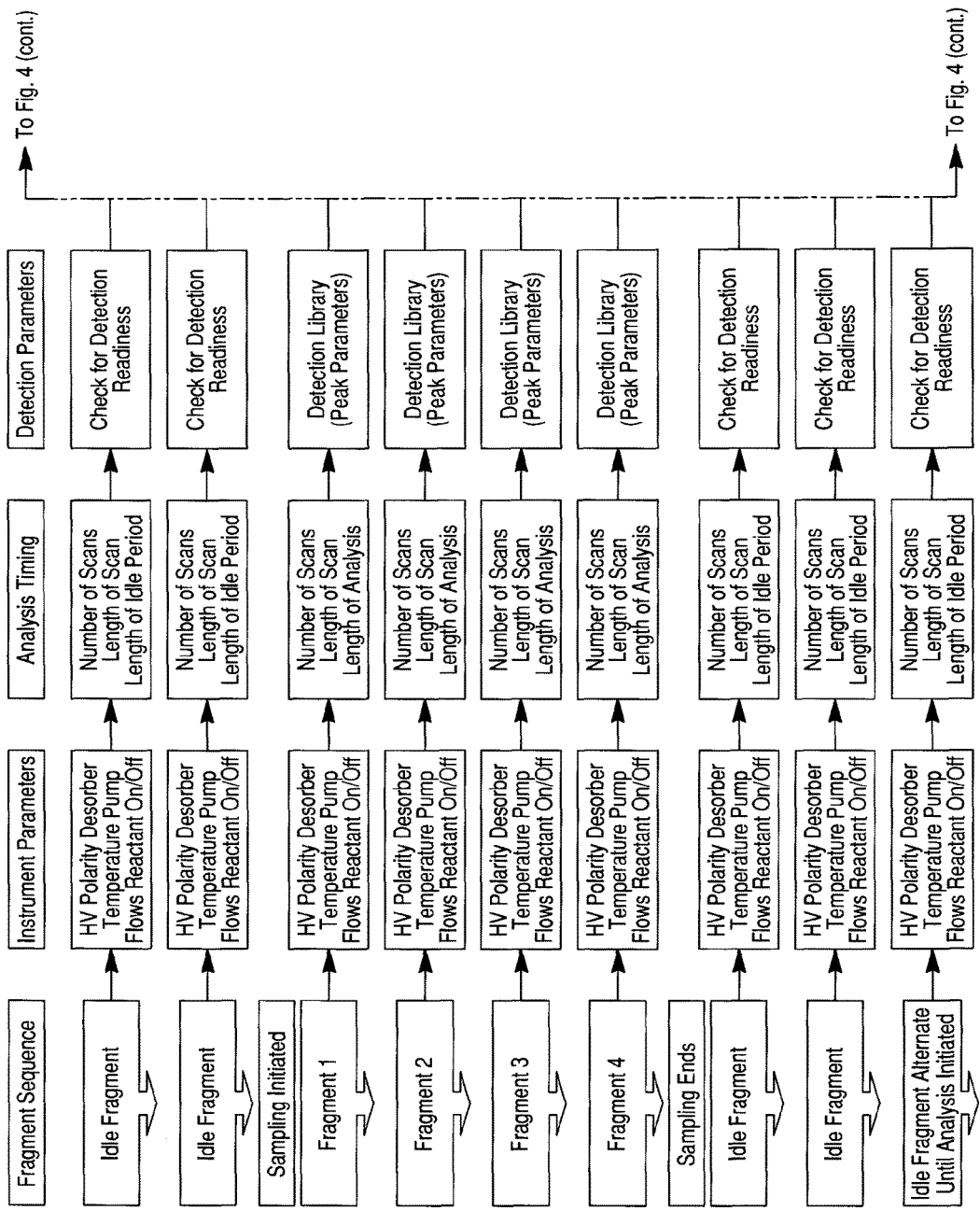
FIG. 4 presents a chart conceptually illustrating an embodiment of the present invention.
Figure 4:
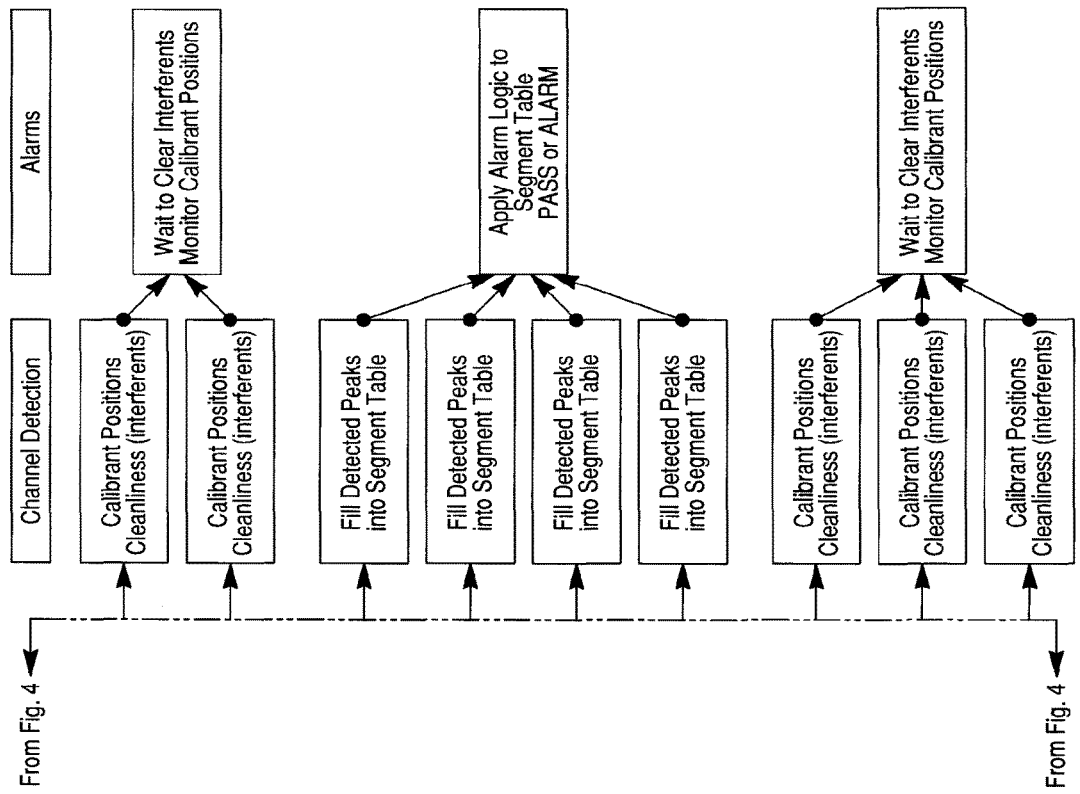

Fragments may be "made" on the remote fragment promulgation unit 1000. FIG. 4 schematically presents how different parameters may be applied to different fragments for use in a substance analysis and/or an idle routine. It can be clearly seen that the fragments may be customized to, in turn, customize/reconfigure the analytical instrument 10.

By using the fragments stored in the DISA 300/adding new fragments to be stored in the DISA 300 as detailed herein, as opposed to utilizing hard-coded data as in the past, the analytical instrument 10 may be easily reconfigured. Once reconfigured, the analytical instrument may operate as detailed herein (e.g., the desorber may be operated (flow rates controlled, setpoints controlled), the IMS gate is opened and shut in a controlled manner, the polarity of the high voltage applied to the drift tube is varied in a controlled manner, reactant flow is controlled, etc.).

Of course, in some embodiments of the present invention, the analytical instrument 10 is reconfigured by storing new fragments into the DISA 400 where previously older fragments were stored. This can be accomplished, in some embodiments, in the field, as opposed to in the initial assembly plant (which is where, in some embodiments, the initial storage of fragments occurs). Once these new fragments are stored, various operational features of the analytical instrument may be changed. For example, instead of the control unit 300 controlling the desorber to operate at an initial desorber setpoint during a given time period during an analysis of a sample substance, once the new fragment(s) are stored in the DISA 400, the control unit 300 controls the desorber to operate at a different setpoint than the initial setpoint during the same time period. This may be the case for other components/functionalities of the instrument 10, which may include, for example, changing the desorber flow rate from that of an initial regime, changing an operation timing of the IMS gate from an initial regime, changing a polarity regime of a high voltage applied to the drift tube from an initial regime, changing a reactant flow regime from an initial regime, etc.

Use of the analytical instrument 10 is concomitant with prior IMS systems, but, instead, in the analytical instrument 10, control is based on fragments, which are used by the control unit 300 to direct the instrument 10 to operate the desorber of the analytical instrument 10 at a desired desorber setpoint and/or a flow rate, operating the IMS gate at a desired timing, varying polarity of the high voltage applied to the drift tube of the IMS at a desired timing, and controlling reactant flow at a desired timing, etc. Once a new fragment(s) is added to the DISA 400, some or all of these operational characteristics may be change.

Some embodiments of the present invention include a program product embedded in a computer-readable medium for reconfiguring an analytical instrument including an ion mobility spectrometer (IMS) and a control unit adapted to control the analytical instrument 10 during a sample substance analysis. The program product includes machine-readable program code(s) on a computer-readable medium including one or more fragments for causing, when executed, the analytical instrument 10 to perform various analysis methods as detailed herein and/or as may be found in typical IMS systems. In some embodiments of the present invention, the machine-readable program code is adapted to be transferred via at least one of an analogue and a digital data communication port onto the DISA 400 which is accessible by the control unit 300, and can be superseded (e.g., be erased, overwritten, relegated to unused status, etc.) by transferring, via at least one of the analogue and the digital communication port onto the data storage unit, a second machine-readable program code different from the first machine readable program code. In some embodiments of the present invention, the program product may include one or more program code(s) storable on the DISA 400 embodying one or more fragments. Indeed, in some embodiments, the program product corresponds to the fragment(s).

Given the disclosure of the present invention, one versed in the art would appreciate that there are other embodiments and modifications within the scope and spirit of the present invention. Accordingly, all modifications attainable by one versed in the art from the present disclosure within the scope and spirit of the present invention are to be included as further embodiments of the present invention.

What is claimed is:

1. An analytical instrument comprising a substance detector configured to perform a chemical analysis on a sample substance, the substance detector including:
   an ion mobility spectrometer (IMS) including an IMS gate and a desorber,
   a control unit, and
   a data input and storage assembly that includes, stored therein:
      a first fragment, the first fragment including a plurality of first analytical instrument control parameters and data defining a first temporal period of a sample substance analysis for which the first analytical instrument control parameters are to be applied, and
      a second fragment, the second fragment including a plurality of second analytical instrument control parameters, and
      a third fragment, the third fragment including a plurality of third analytical instrument control parameters,
   wherein the control unit is configured to control, during the first temporal period of the sample substance analysis, operational functionality of the analytical instrument based on at least the stored first fragment, and
   wherein the control unit is configured to evaluate data obtained during the first temporal period and, based on data obtained during the first temporal period, select either the stored second fragment or the stored third fragment to control, during a second temporal period, the operational functionality of the analytical instrument based on the stored second fragment or the stored third fragment, wherein the second temporal period is later than the first temporal period and defined by temporal data included in the selected one of the stored second fragment or the stored third fragment,
   wherein each of the first, second, and third fragments includes, among the plurality of analytical instrument control parameters:
      a desorber setpoint control parameter to control a setpoint of the desorber, and
      an IMS gate width timing control parameter to control to control IMS gate width timing of the IMS gate to control sensitivity and/or resolution during operation of the analytical instrument.

2. The analytical instrument of claim 1, wherein the setpoint of the desorber setpoint control parameter of the second fragment is different than the setpoint of the desorber setpoint control parameter of the first fragment.

3. The analytical instrument of claim 1,
   wherein the setpoint of the desorber setpoint control parameter of the second fragment is different than the setpoint of the desorber setpoint control parameter of the first fragment, and
   wherein the IMS gate width timing of the IMS gate width timing control parameter of the second fragment is different than the IMS gate width timing of the IMS gate width timing control parameter of the first fragment.

4. The analytical instrument of claim 1,
   wherein each of the first, second, and third fragments includes, among the plurality of analytical instrument control parameters, one or more of:
      a control parameter to control desorber flow of the desorber during operation of the analytical instrument;
      a control parameter to control a polarity of a voltage applied to a drift tube of the ion mobility spectrometer during operation of the analytical instrument;
      a control parameter to control usage of a reactant during operation of the analytical instrument;
      a control parameter to control a sample substance purge cycle during operation of the analytical instrument;
      a control parameter to control the analytical instrument to collect data during the sample substance purge cycle to verify whether the sample substance has been sufficiently purged from a test location of the substance detector of the analytical instrument; and
      a control parameter to control the analytical instrument to perform a diagnostic routine, the diagnostic routine including a routine enabling the analytical instrument to make a determination of whether the reactant is present.

5. The analytical instrument of claim 4,
   wherein the plurality of respective analytical instrument control parameters of the first, second, and third fragments include a control parameter to control desorber flow of the desorber during operation of the analytical instrument while switching polarity of the voltage applied to the drift tube during an analysis of a sample substance.

6. The analytical instrument of claim 1,
   wherein the analytical instrument is configured to operate according to an operational regime,
   wherein operation of the analytical instrument in the operational regime includes a sample substance analysis operation and an idle operation, and
   wherein the analytical instrument is configured to selectively implement various of the analytical instrument control parameters depending on whether the analytical instrument is undertaking the sample substance analysis operation or undertaking the idle operation, and
   wherein, when the analytical instrument is undertaking an idle operation, the analytical instrument analyzes a calibration substance for calibration purposes, the calibration substance being separate from the sample substance.

7. The analytical instrument of claim 1, wherein the analytical instrument includes an IMS drift tube, and wherein the control unit is configured to adjust an absolute value of a high voltage applied to the drift tube.

8. The analytical instrument of claim 1, wherein:
   the substance detector includes an IMS drift tube, the substance detector being configured to switch, during an analysis of the sample substance, polarities of a high voltage applied to the drift tube according to a polarity switching regime, the polarity switching regime being based on one or more analytical instrument control parameters of at least one of the first fragment and the second fragment;
   the analytical instrument is configured to vary a prestored temperature ramping regime of the desorber, wherein the control unit is configured to control desorber temperature to achieve one or more temperatures during a sample analysis time period according to a prestored temperature ramping regime, the prestored temperature ramping regime being stored in the data input and storage assembly and being based on one or more analytical instrument control parameters of at least one of the first fragment and the second fragment;

the analytical instrument is configured to operate according to at least one prestored desorber flow control regime, wherein the control unit is configured to control a desorber flow according to the at least one prestored desorber flow control regime to achieve one or more desorber flows during the sample analysis time period, the at least one prestored desorber flow control regime being stored in the data input and storage assembly and being based on one or more analytical instrument control parameters of at least one of the first fragment and the second fragment;

the analytical instrument is configured to operate according to at least one prestored reactant flow control regime the control unit is configured to control a reactant flow according to the at least one prestored reactant flow control regime to selectively permit reactant flow and halt the reactant flow during the analysis of the sample substance, the at least one prestored reactant flow control regime being stored in the data input storage assembly and being based on one or more analytical instrument control parameters of at least one of the first fragment and the second fragment; and the analytical instrument is configured to operate according to at least one prestored purge control regime, wherein the analytical instrument purges a sample substance containment area of effectively all sample substance according to the at least one prestored purge control regime, the at least one prestored purge control regime being stored in the data input and storage assembly and being based on one or more analytical instrument control parameters of at least one of the first fragment and the second fragment.

9. The analytical instrument of claim 1, wherein the substance detector further comprises:
a swab interface;
a desorber assembly, wherein the desorber assembly includes a heat transfer device configured to heat the desorber, and wherein the desorber assembly includes a gas supply configured to direct gas through the desorber,
a drift tube;
a high voltage device arrayed, at least in part, proximate to the drift tube, wherein the high voltage device is configured to change a polarity of a voltage applied to the drift tube and have a voltage gradient of the drift tube of about 100 to 500 volts per centimeter; and
a reactant supply unit configured to supply reactant during a sample substance analysis.

10. The analytical instrument of claim 1,
wherein the substance detector further includes at least one of an analogue and a digital data communication interface,
wherein the data input and storage assembly is configured to receive and store at least one new fragment via the at least one of an analogue and a digital data communication interface, and
wherein the control unit is further configured to, after the at least one new fragment is received and stored by the data input and storage assembly, control the operational functionality of the analytical instrument based on at least the at least one new fragment.

11. The analytical instrument of claim 1, wherein the first temporal period and the second temporal period are temporal periods of a single sample substance analysis.

12. An analytical instrument comprising a substance detector configured to perform a chemical analysis on a sample substance, the substance detector including:
a control unit; and
a data input and storage assembly that includes, stored therein:
a first fragment, the first fragment including a first analytical instrument control parameter and data defining a first temporal period of a sample substance analysis for which the first analytical instrument control parameter is to be applied, and
a second fragment, the second fragment including a second analytical instrument control parameter and data defining a second temporal period of a sample substance analysis for which the second analytical instrument control parameter is to be applied;
wherein the control unit is configured to control, during the first temporal period of the sample substance analysis, operational functionality of the analytical instrument based on at least the stored first fragment;
wherein the control unit is configured to control, during the second temporal period later than the first temporal period, the operational functionality of the analytical instrument based on at least the stored second fragment;
wherein the substance detector includes a desorber;
wherein the substance detector includes an IMS drift tube, the substance detector being configured to switch, during an analysis of the sample substance, polarities of a high voltage applied to the drift tube according to a polarity switching regime, the polarity switching regime being based on one or more analytical instrument control parameters of at least one of the first fragment and the second fragment;
wherein the analytical instrument is configured to vary a temperature ramping regime of the desorber, wherein the control unit is configured to control desorber temperature to achieve one or more temperatures during a sample analysis time period according to a prestored temperature ramping regime, the prestored temperature ramping regime being stored in the data input and storage assembly and being based on one or more analytical instrument control parameters of at least one of the first fragment and the second fragment;
wherein the analytical instrument is configured to operate according to at least one prestored desorber flow control regime, wherein the control unit is configured to control a desorber flow according to the at least one prestored desorber flow control regime to achieve one or more desorber flows during the sample analysis time period, the at least one prestored desorber flow control regime being stored in the data input and storage assembly and being based on one or more analytical instrument control parameters of at least one of the first fragment and the second fragment;
wherein the analytical instrument is configured to operate according to at least one prestored reactant flow control regime, wherein the control unit is configured to control a reactant flow according to the at least one prestored reactant flow control regime to selectively permit reactant flow and halt the reactant flow during the analysis of the sample substance, the at least one stored prestored reactant flow control regime being stored in the data input storage assembly and being based on one or more analytical instrument control parameters of at least one of the first fragment and the second fragment; and wherein the analytical instrument is configured to operate according to at least one prestored purge control regime, wherein the analytical instrument purges a sample substance containment area effectively of effectively all sample substance according to the at least one prestored purge control regime, the at least one prestored purge control regime being stored in the data input and storage assembly and being based on one or more analytical instrument control parameters of at least one of the first fragment and the second fragment.

* * * * *